(12) United States Patent
Parker et al.

(10) Patent No.: US 7,462,736 B2
(45) Date of Patent: *Dec. 9, 2008

(54) METHODS AND APPARATUS FOR ISOLATING CARBOXYLIC ACID

(75) Inventors: Kenny Randolph Parker, Afton, TN (US); Philip Edward Gibson, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/708,200

(22) Filed: Feb. 20, 2007

(65) Prior Publication Data

US 2007/0208198 A1    Sep. 6, 2007

Related U.S. Application Data

(60) Provisional application No. 60/777,893, filed on Mar. 1, 2006, provisional application No. 60/777,799, filed on Mar. 1, 2006, provisional application No. 60/777,809, filed on Mar. 1, 2006, provisional application No. 60/777,810, filed on Mar. 1, 2006, provisional application No. 60/777,902, filed on Mar. 1, 2006.

(51) Int. Cl.
    *C07C 51/42*   (2006.01)
(52) U.S. Cl. .................................................. 562/485
(58) Field of Classification Search ................. 562/485
    See application file for complete search history.

(56) References Cited

U.S. PATENT DOCUMENTS

| | | | |
|---|---|---|---|
| 4,158,738 A | 6/1979 | Scott et al. | |
| 4,219,669 A | 8/1980 | Tsuchiya et al. | |
| 4,330,676 A | 5/1982 | Moxham | |
| 4,356,319 A | 10/1982 | Roffia et al. | |
| 4,769,489 A | 9/1988 | Abrams et al. | |
| 4,792,621 A | 12/1988 | Abrams | |
| 4,914,230 A | 4/1990 | Abrams et al. | |
| 4,939,297 A | 7/1990 | Browder et al. | |
| 5,175,355 A | 12/1992 | Streich et al. | |
| 5,470,473 A | 11/1995 | Park et al. | |
| 5,583,254 A | 12/1996 | Turner | |
| 5,643,468 A | 7/1997 | Ure | |
| 5,676,847 A | 10/1997 | Yamamoto | |
| 5,698,734 A * | 12/1997 | Turner et al. ................ | 562/412 |
| 5,705,682 A | 1/1998 | Ohkashi et al. | |
| 5,770,765 A | 6/1998 | Ohkashi | |
| 5,840,965 A | 11/1998 | Turner et al. | |
| 5,877,346 A | 3/1999 | Hindmarsh et al. | |
| 5,971,907 A | 10/1999 | Johannemann et al. | |
| 6,150,553 A | 11/2000 | Parten | |
| 6,307,099 B1 | 10/2001 | Turner et al. | |
| 6,355,835 B1 * | 3/2002 | Kulsrestha et al. .......... | 562/417 |
| 6,562,997 B2 | 5/2003 | Sikkenga et al. | |
| 6,639,104 B2 | 10/2003 | Piras et al. | |
| 6,655,531 B1 | 12/2003 | Beard et al. | |
| 6,765,113 B2 | 7/2004 | Graham et al. | |
| 7,074,954 B2 | 7/2006 | Sheppard et al. | |
| 7,132,566 B2 | 11/2006 | Sumner, Jr. et al. | |
| 7,193,109 B2 * | 3/2007 | Lin et al. ..................... | 562/485 |
| 2002/0016500 A1 | 2/2002 | Matsumoto et al. | |
| 2003/0004372 A1 | 1/2003 | Piras et al. | |
| 2004/0110980 A1 | 6/2004 | Sheppard et al. | |
| 2004/0244536 A1 | 12/2004 | Lin | |
| 2004/0245176 A1 | 12/2004 | Parker et al. | |
| 2004/0249208 A1 | 12/2004 | Lin et al. | |
| 2005/0159578 A1 | 7/2005 | Parker et al. | |
| 2005/0283022 A1 | 12/2005 | Sheppard | |
| 2006/0047165 A1 | 3/2006 | Lin et al. | |
| 2007/0205153 A1 * | 9/2007 | Parker et al. ................ | 210/634 |
| 2007/0208199 A1 * | 9/2007 | Parker et al. ................ | 562/485 |
| 2007/0208200 A1 * | 9/2007 | Parker et al. ................ | 562/485 |

FOREIGN PATENT DOCUMENTS

| | | |
|---|---|---|
| DE | 10 2004002962 | 8/2005 |
| EP | 0406424 | 1/1991 |
| EP | 0630673 | 12/1994 |
| WO | WO 00/63146 | 10/2000 |
| WO | WO 01/49647 | 7/2001 |
| WO | WO 01/55075 | 8/2001 |

OTHER PUBLICATIONS

Copending U.S. Appl. No. 11/708,245, filed Feb. 20, 2007, Kenny Randolph Parker et al.
Copending U.S. Appl. No. 11/705,330, filed Feb. 12, 2007, Philip Edward Gibson et al.
Copending U.S. Appl. No. 11/705,307, filed Feb. 12, 2007, Philip Edward Gibson et al.
PCT International Search Report for corresponding application.

* cited by examiner

*Primary Examiner*—Sikarl A Witherspoon
(74) *Attorney, Agent, or Firm*—Steven A. Owen; Bernard J. Graves, Jr.

(57) ABSTRACT

Disclosed are methods and apparatus for isolating a carboxylic acid. The processes employ a rotary pressure drum filter as a product isolation device in a carboxylic acid production process. The product isolation device is employed to isolate purified carboxylic acid particles from an isolation feed slurry comprising an aliphatic acid.

21 Claims, 5 Drawing Sheets

METHODS AND APPARATUS FOR ISOLATING CARBOXYLIC ACID

RELATED APPLICATIONS

Figure 1:
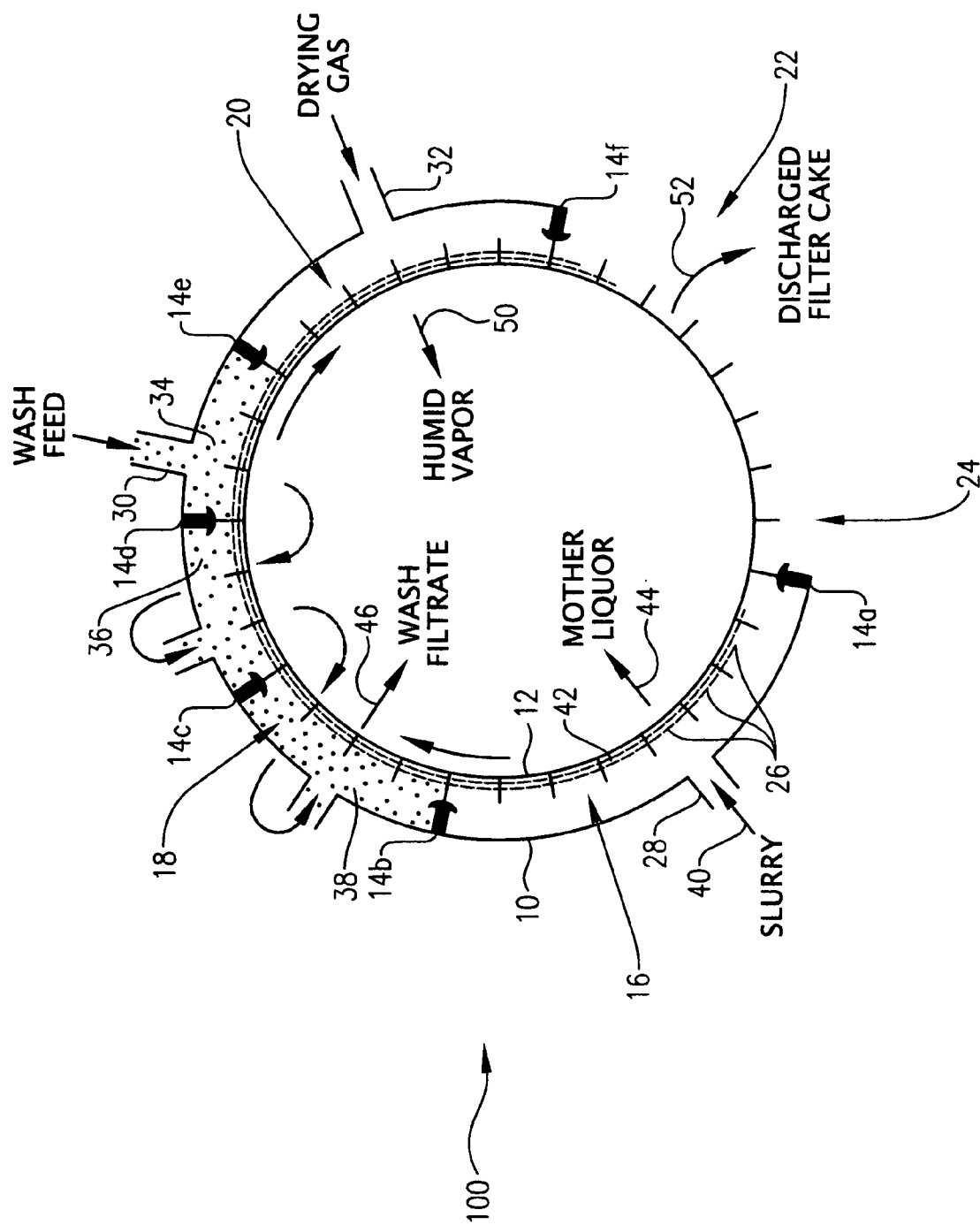

This application claims the priority benefit of U.S. Provisional Pat. App. Ser. Nos. 60/777,893; 60/777,799; 60/777,809; 60/777,810; and 60/777,902, all filed Mar. 1, 2006, the entire disclosures of which are incorporated herein by reference.

BACKGROUND OF THE INVENTION

1. Field of the Invention

The present invention relates generally to a product isolation process for use in various carboxylic acid production processes. More specifically, the present invention concerns equipment and processes for isolating purified carboxylic acid particles from a slurry comprising an aliphatic acid.

2. Description of the Prior Art

In conventional terephthalic acid (TPA) production processes, para-xylene undergoes oxidation to form crude terephthalic acid (CTA) particles. A slurry of CTA particles can then undergo purification to form purified terephthalic acid (PTA) particles. A purified slurry comprising PTA particles and a liquid phase can then be treated in a product isolation zone to isolate at least a portion of the PTA particles. In some cases, the liquid phase of the purified slurry comprises oxidation byproducts formed from the oxidation of para-xylene.

Various techniques are known in the art for isolating PTA particles from a purified slurry. An example of one such technique includes the use of a vacuum filter. Vacuum filters typically employ a filter cloth through which the liquid phase of the slurry is drawn using a vacuum source, thus leaving a filter cake of PTA particles on the cloth. However, conventional techniques for isolating PTA can be problematic when the liquid phase of the purified slurry contains oxidation byproducts, due to the tendency of such oxidation byproducts to precipitate onto the filter cloth. Such precipitation can foul the filter cloth thereby reducing the filtration rate. Additionally, filter surfaces and conduits that the liquid phase contacts after exiting the filter cloth can also become coated with oxidation byproducts and eventually plug with solids. Accordingly, there is a need for methods and/or equipment that can reduce oxidation byproduct precipitation during PTA isolation.

SUMMARY OF THE INVENTION

One embodiment of the present invention concerns a method for isolating purified particles comprising an aromatic dicarboxylic acid. The method of this embodiment comprises: treating an isolation feed slurry comprising the purified particles in a product isolation zone to thereby produce a wet cake comprising the aromatic dicarboxylic acid in an amount of at least about 10 weight percent, wherein the product isolation zone is defined within a rotary pressure drum filter, and wherein the slurry comprises an aliphatic acid in an amount of at least about 10 weight percent.

Another embodiment of the present invention concerns a method for isolating purified terephthalic acid (PTA) particles. The method of this embodiment comprises: (a) introducing an isolation feed slurry comprising the PTA particles and a liquid phase into a product isolation zone; (b) removing at least a portion of the liquid phase to thereby produce a wet cake and a mother liquor; and (c) routing at least a portion of the mother liquor to a purge treatment zone, wherein the product isolation zone is defined within a rotary pressure drum filter, and wherein the liquid phase comprises an aliphatic acid in an amount of at least about 10 weight percent.

Still another embodiment of the present invention concerns a process for producing purified terephthalic acid (PTA). The process of this embodiment comprises: (a) oxidizing an aromatic compound in an oxidation zone to thereby produce a crude slurry comprising crude terephthalic acid (CTA) particles; (b) subjecting at least a portion of the crude slurry to purification to thereby produce a purified slurry comprising PTA particles, oxidation byproducts, and an aliphatic acid in an amount of at least about 10 weight percent; and (c) isolating at least a portion of the PTA particles from the purified slurry in a product isolation zone to thereby produce a PTA product, wherein the product isolation zone is defined within a rotary pressure drum filter, wherein the cumulative rate at which the oxidation byproducts exit the PTA production process with the PTA product and/or are combined with the PTA product downstream of the PTA production process is at least about 15 percent of the net make rate of the oxidation byproducts in the PTA production process.

Yet another embodiment of the present invention concerns a method for treating a purified slurry comprising purified terephthalic acid (PTA) particles. The method of this embodiment comprises: treating the purified slurry in a catalyst removal zone to thereby produce a wet cake comprising at least a portion of the PTA particles and a mother liquor, wherein the slurry comprises the PTA particles in an amount of at least about 15 weight percent, wherein the slurry comprises acetic acid, and wherein the catalyst removal zone is defined within a rotary pressure drum filter.

BRIEF DESCRIPTION OF THE DRAWING FIGURES

Figure 2:
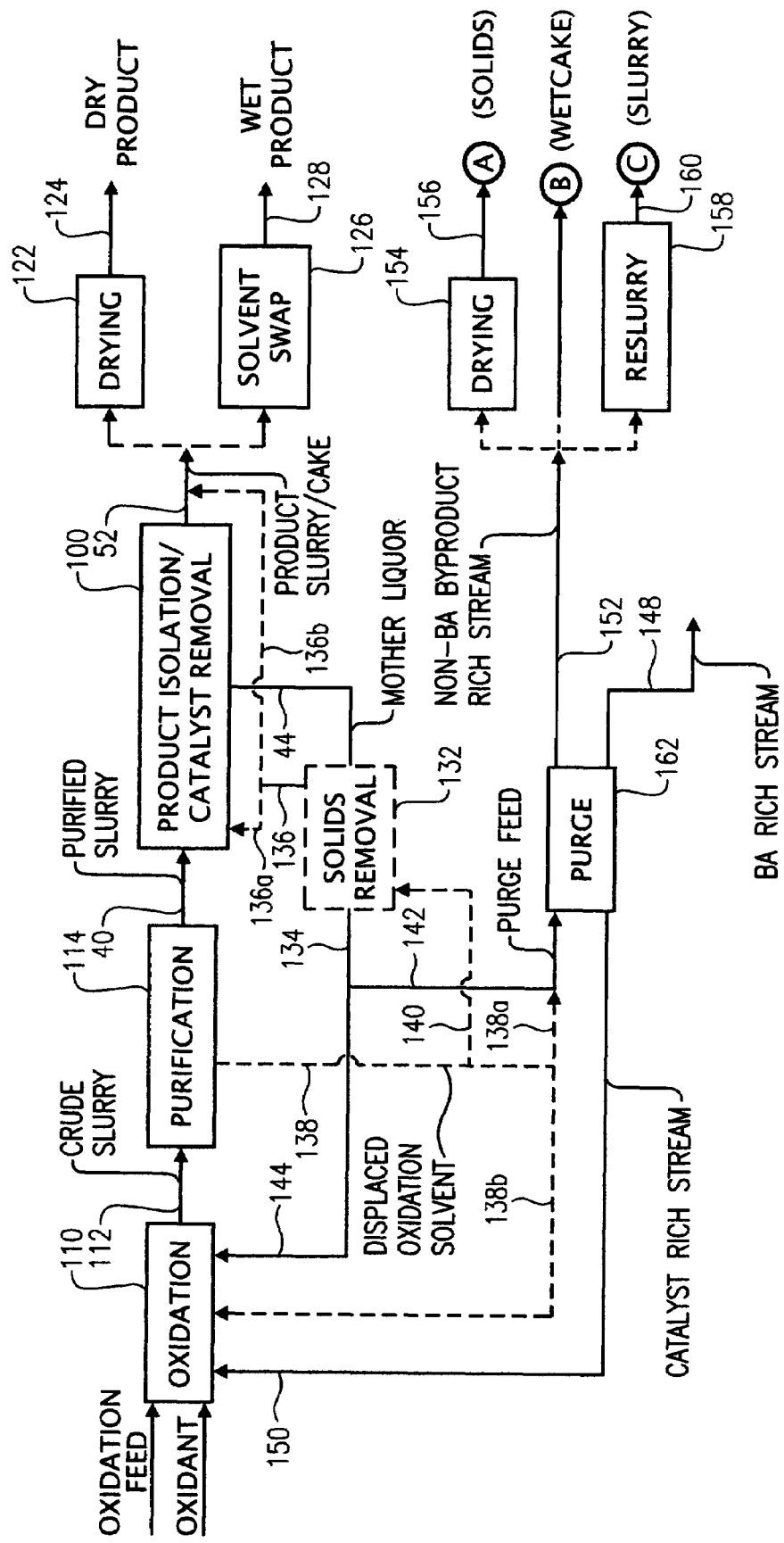
Figure 3:
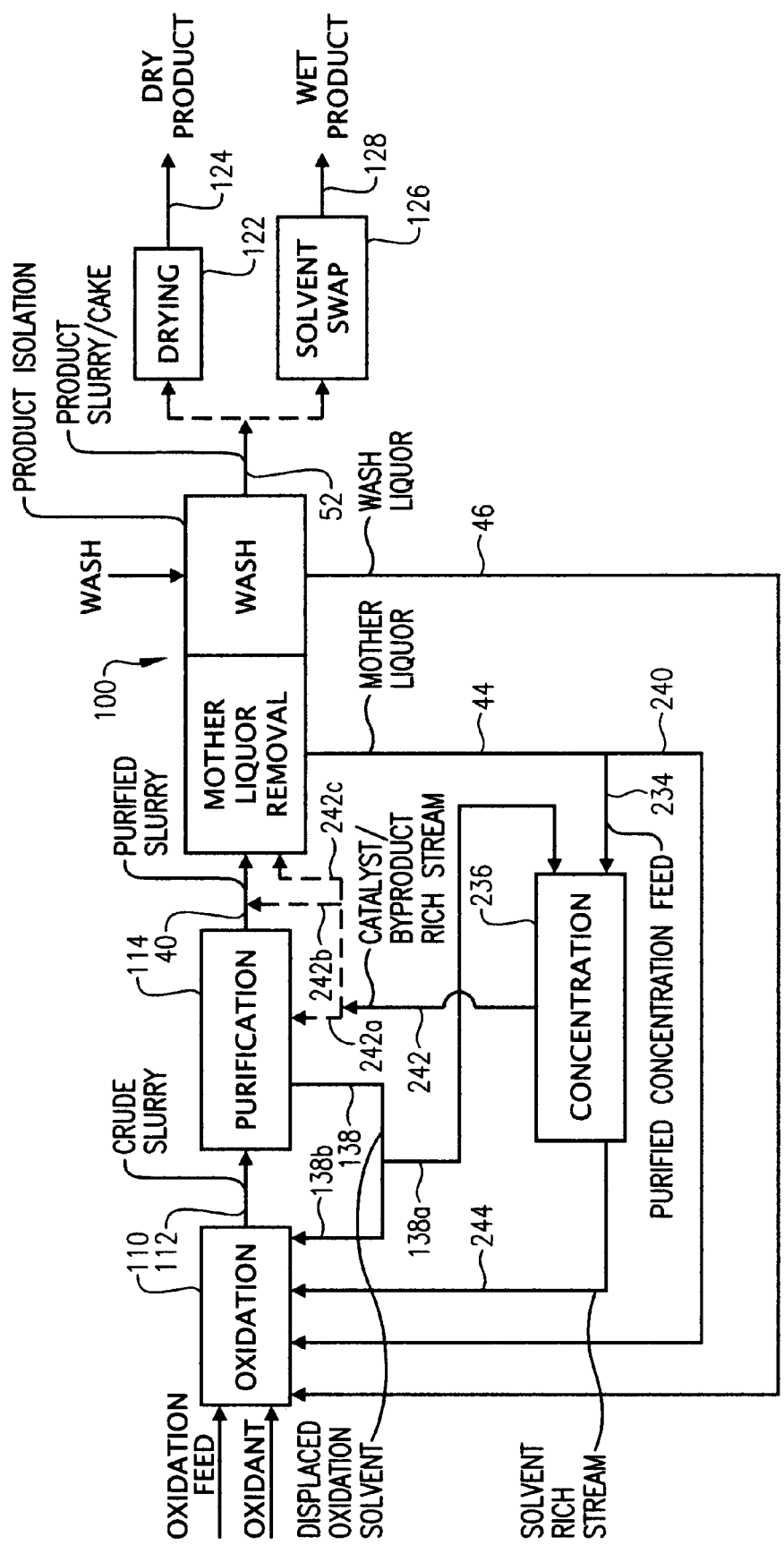
Figure 4:
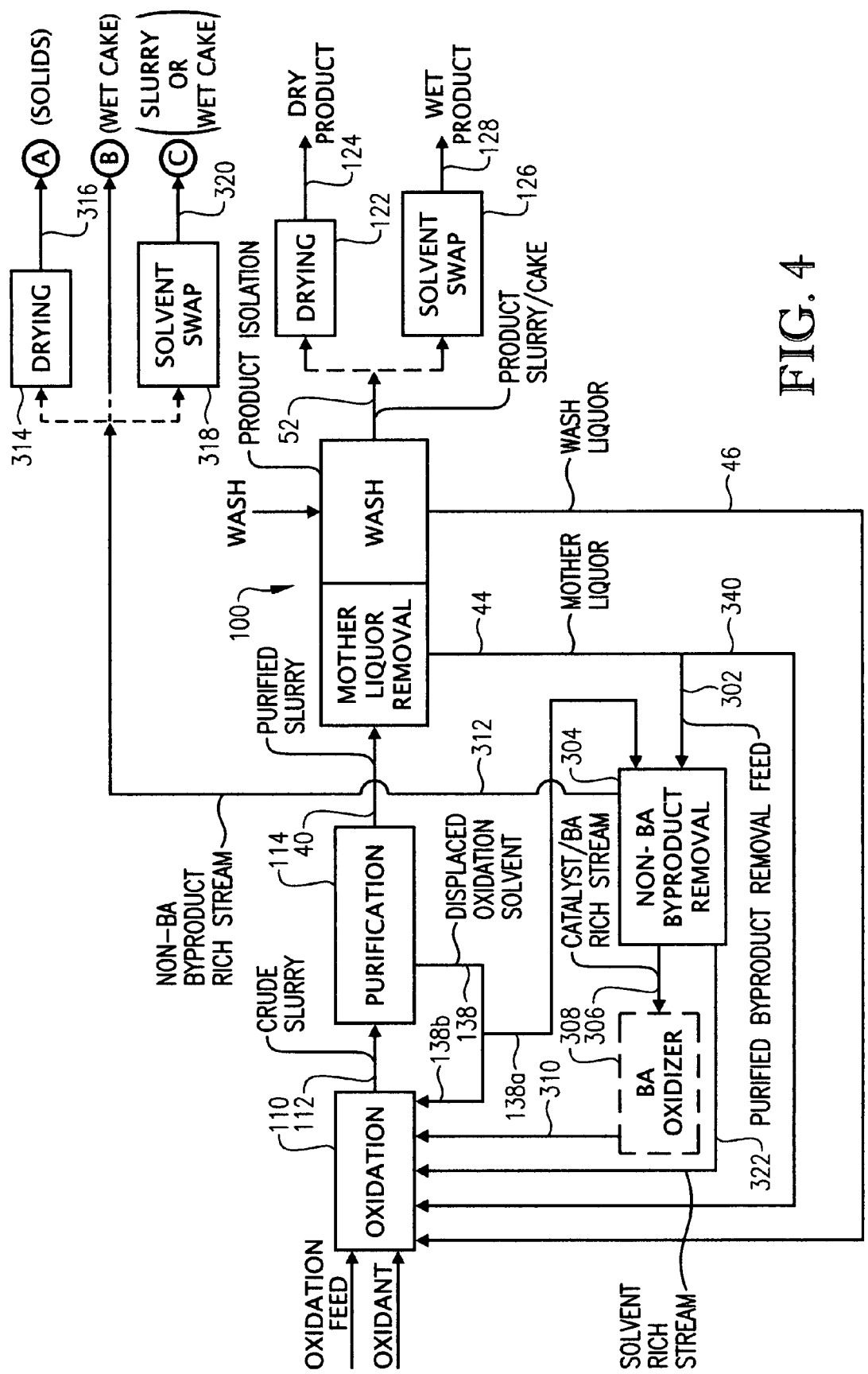
Figure 5:
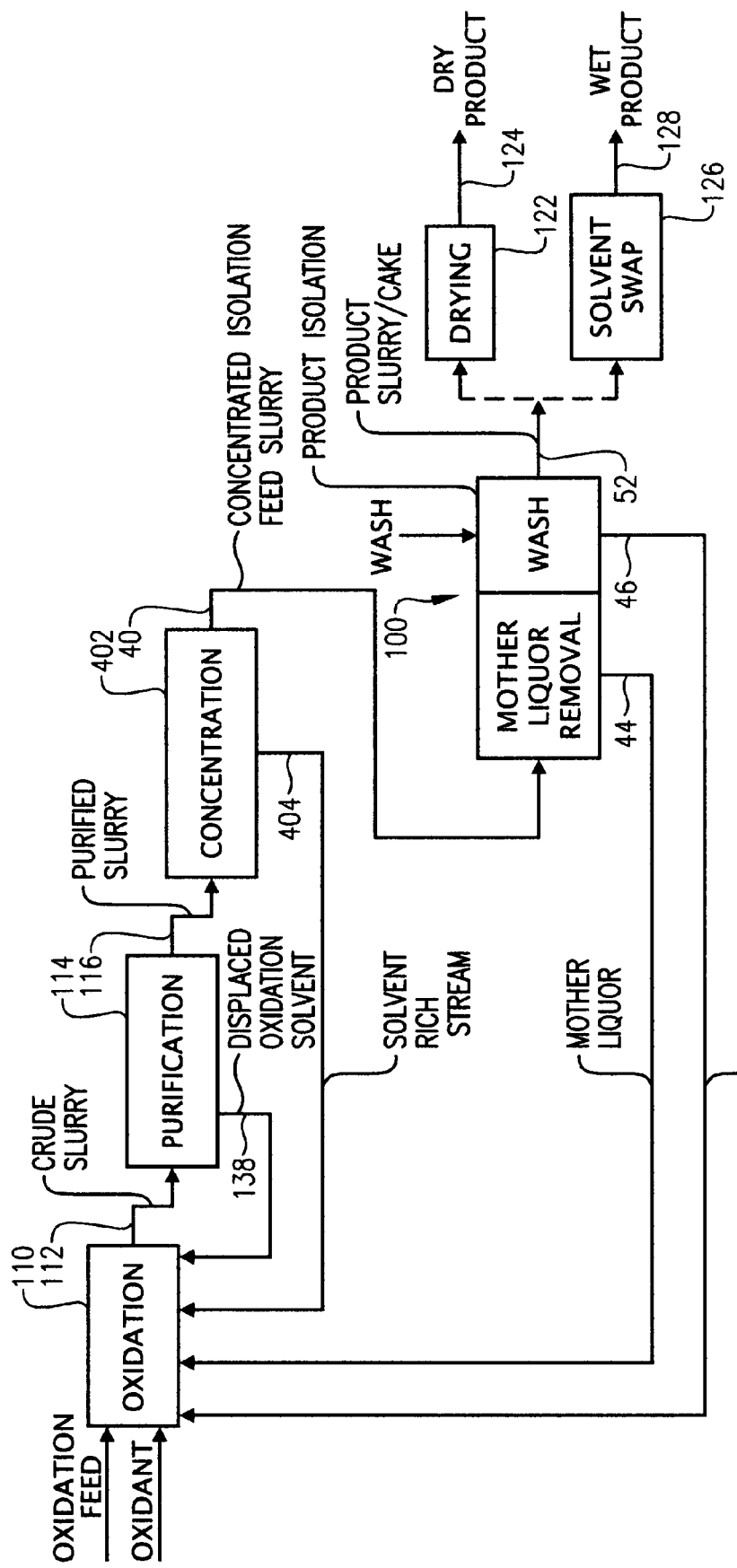

A preferred embodiment of the present invention is described in detail below with reference to the attached drawing figures, wherein:

FIG. 1 is a schematic representation of a rotary pressure drum filter that can be employed to isolate carboxylic acid from the liquid phase of a slurry produced by one or more oxidation reactors;

FIG. 2 is a process flow diagram illustrating a system for the production and purification of carboxylic acid constructed in accordance with the present invention, particularly illustrating a configuration where the crude slurry from the oxidation reactor is subjected to purification, the resulting purified slurry is subjected to product isolation, and a portion of the mother liquor from the product isolation zone is employed as a feed to a purge treatment system;

FIG. 3 is a process flow diagram illustrating a system for the production and purification of carboxylic acid constructed in accordance with the present invention, particularly illustrating a configuration where the crude slurry from the oxidation reactor is subjected to purification, the resulting purified slurry is subjected to product isolation, and a portion of the mother liquor from the product isolation zone is employed as a feed to a concentration zone;

FIG. 4 is a process flow diagram illustrating a system for the production and purification of carboxylic acid constructed in accordance with the present invention, particularly illustrating a configuration where the crude slurry from the oxidation reactor is subjected to purification, the resulting purified slurry is subjected to product isolation, and a portion of the mother liquor from the product isolation zone is employed as a feed to a non-benzoic acid (non-BA) byproduct removal zone; and FIG. 5 is a process flow diagram illustrating a system for the production and purification of carboxylic acid constructed in accordance with the present invention, particularly illustrating a configuration where the crude slurry from the oxidation reactor is subjected to purification, the resulting purified slurry is subjected to concentration, the resulting solvent rich stream is returned to the oxidation reactor and the resulting concentrated isolation feed slurry is subjected to product isolation.

DETAILED DESCRIPTION

In accordance with one embodiment of the present invention, an isolation feed slurry comprising carboxylic acid and oxidation byproducts can be treated in a product isolation zone. The product isolation zone can separate the isolation feed slurry into a primarily fluid phase mother liquor and a primarily solid phase isolated product wet cake comprising isolated solids.

In one embodiment of the present invention, a product isolation zone 100 of a carboxylic acid production process can be defined within a rotary pressure drum filter, similar to the device depicted in FIG. 1. In one embodiment, the product isolation zone can be a catalyst removal zone defined within a rotary pressure filter. As used herein, the term "rotary pressure drum filter" denotes a device that uses a pressure differential across a rotating drum filter to facilitate solid/liquid separation. The rotary pressure drum filter depicted in FIG. 1 comprises a housing 10 and a rotary drum filter 12 rotatably disposed within housing 10. An annulus is defined between the inside of housing 10 and the outside of rotary drum filter 12. This annulus is divided into various discreet zones by seals 14a, b, c, d, e, f. A filtration zone 16 can be defined in the annulus between seals 14a and 14b. A wash zone 18 can be defined in the annulus between seals 14b and 14e. A dewatering/drying zone 20 can be defined in the annulus between seals 14e and 14f. Housing 10 can be open between seals 14f and 14a. This open portion of housing 10 can include a discharge zone 22 and a cloth wash zone 24.

Referring still to FIG. 1, rotary drum filter 12 can define a plurality of filter cells 26 located on the periphery of the drum. The bottom of each filter cell 26 is formed of a filter media (e.g., synthetic cloth, single-layer metal, or multi-layer metal). Fluid flow through the filter media can be caused by creating a pressure differential across the filter media. Each filter cell 26 has its own outlet for discharging fluids inwardly towards the axis of rotation of rotary drum filter 12. The outlets of axially-aligned filter cells 26 are manifolded. The manifolds (not shown) rotate with the rotary drum filter 12 and communicate with a service/control head (not shown) which collects the fluids from the manifolds in a manner that allows the fluids discharged from zones 16, 18, and 20 to be kept separate.

Housing 10 can define an isolation feed slurry inlet 28 that can communicate with filtration zone 16, a wash feed inlet 30 that can communicate with wash zone 18, and a drying gas inlet 32 that can communicate with dewatering/drying zone 20. Wash zone 18 can be divided into an initial wash zone 34, an intermediate wash zone 36, and a final wash zone 38 by seals 14c and 14d. Housing 10 and rotary drum filter 12 can be configured to permit filtrate discharged from initial wash zone 34 to enter intermediate wash zone 36, and filtrate discharged from intermediate wash zone 36 to enter final wash zone 38.

In operation, an isolation feed slurry in line 40 can enter filtration zone 16 via slurry inlet 28. The isolation feed slurry in line 40 can comprise solid particles and a liquid phase comprising an aliphatic acid. In one embodiment, the isolation feed slurry in line 40 can comprise aliphatic acid in an amount of at least about 10 weight percent, at least about 30 weight percent, or at least 50 weight percent. Additionally, the liquid phase of the isolation feed slurry can comprise aliphatic acid in an amount of at least about 60 weight percent, at least about 75 weight percent, or at least 85 weight percent. The aliphatic acid can comprise an aliphatic carboxylic acid having from 1 to 6 carbon atoms. In one embodiment, the aliphatic acid can comprise acetic acid. Furthermore, the liquid phase of the isolation feed slurry can comprise water.

In one embodiment, the isolation feed slurry can comprise solid particles in an amount in the range of from about 1 to about 50 weight percent, in the range of from about 5 to about 40 weight percent, or in the range of from 20 to 35 weight percent. The solid particles in the isolation feed slurry can have a mean particle size of at least about 40 microns, in the range of from about 50 to about 2,000 microns, or in the range of from 60 to 200 microns. Additionally, the solid particles in the isolation feed slurry can comprise a carboxylic acid. In one embodiment, the solid particles can have an average concentration of carboxylic acid of at least about 50 weight percent, at least about 75 weight percent, or at least 95 weight percent. Also, the solid particles can be purified particles such as purified terephthalic acid (PTA) particles. In one embodiment, the solid particles can comprise 4-carboxybenzaldehyde (4-CBA) in an amount of less than about 400 ppmw, less than about 250 ppmw, or in the range of form 10 to 200 ppmw. Other possible variations in the composition of the isolation feed slurry in line 40 will be discussed in greater detail below with reference to FIGS. 2-5, along with possible sources of the isolation feed slurry.

The isolation feed slurry introduced into filtration zone 16 can form a filter cake (i.e., a wet cake) 42 in filter cells 26 on the periphery of rotary filter drum 12. In filtration zone 16, a predominately fluid phase mother liquor can be discharged radially inward from the bottom of each filter cell 26. The mother liquor collected from filtration zone 16 can be discharged from the apparatus via line 44. Upon obtaining a desired height of filter cake 42 in filtration zone 16, rotary drum filter 12 can rotate so that filter cake 42 enters wash zone 18.

In wash zone 18, filter cake 42 can be washed with a wash feed entering initial wash zone 34 via wash feed inlet 30. The wash feed can comprise acetic acid and/or water. Furthermore, the wash feed can have a temperature in the range of from about the freezing point of the wash feed to about the boiling point of the wash feed, in the range of from about 20 to about 110° C., or in the range of from 40 to 90° C. The wash filtrate from initial wash zone 34 can then be transferred to intermediate wash zone 36, and the wash filtrate from intermediate wash zone 36 can then be transferred to final wash zone 38. The wash filtrate (i.e., wash liquor) can then be discharged from product isolation zone 100 via line 46. In one embodiment of the present invention, the wash filtrate in line 46 can be combined into the mother liquor in line 44. After suitable washing in wash zone 18, rotary drum filter 12 can rotate so that washed filter cake 42 can enter dewatering/drying zone 20.

In dewatering/drying zone 20, liquid can be removed from washed filter cake 42 by passing a drying gas, entering via gas inlet 32, through washed filter cake 42. The drying gas introduced into inlet 32 can comprise nitrogen, carbon dioxide, and/or process off-gases. As used herein, the term "process off-gas" is defined as a gas which was used in the oxidation step of a carboxylic acid production process. Liquid removed from washed filter cake 42 can exit product isolation zone 100 via line 50, and can exit in a liquid phase and/or a vapor phase. Additionally, the gas stream passed through washed filter cake 42 can exit product isolation zone 100 as a humid vapor via line 50. After filter cake 42 is dewatered/dried in zone 20, rotary drum filter 12 can rotate so that dried filter cake 42 enters discharge zone 22.

In discharge zone 22, at least a portion of filter cake 42 can be disengaged from rotary drum filter 12 and can exit product isolation zone 100 via line 52. Rotary drum filter 12 can then rotate into cloth wash zone 24, where any solid particles remaining in filter cells 26 can be removed.

In one embodiment, filter cake (i.e., isolated product) 42 discharged via line 52 can comprise at least about 10 weight percent of the above-mentioned carboxylic acid. Furthermore, the filter cake in line 52 can comprise the above-mentioned solid particles (e.g., PTA particles) in an amount in the range of from about 70 to about 95 weight percent, in the range of from about 75 to about 90 weight percent, or in the range of from 77 to 88 weight percent. Other possible variations in the composition of the isolated product discharged via line 52 will be discussed in greater detail below with reference to FIGS. 2-5, along with possible treatment options for the isolated product.

An example of a suitable commercially available rotary pressure drum filter which can be employed in product isolation zone 100 includes, but is not limited to, a BHS-FEST ROTARY PRESSURE FILTER, available from BHS-Sonthofen GmbH, D-87527, Sonthofen, Germany.

FIG. 2 illustrates one embodiment of the present invention where the product isolation device discussed above with reference to FIG. 1 can be employed in a carboxylic acid production process where carboxylic acid produced in an oxidation reactor and purified in a purification reactor is subjected to product isolation in product isolation zone 100. As used herein, a "carboxylic acid production process" and a "TPA production process" are defined as beginning with an initial oxidation step and ending with an isolated product, and can include therein one or more purification steps, concentration steps, isolation steps, purge steps, and/or additional oxidation steps.

In the embodiment illustrated in FIG. 2, a predominately fluid-phase feed stream containing an oxidizable compound (e.g., para-xylene), a solvent (e.g., acetic acid and/or water), and a catalyst system (e.g., cobalt, manganese, and/or bromine) can be introduced into oxidation zone 110. A predominately gas-phase oxidant stream containing molecular oxygen can also be introduced into oxidation zone 110. The fluid- and gas-phase feed streams form a multi-phase reaction medium in oxidation zone 110. The oxidizable compound can undergo partial oxidation in a liquid phase of the reaction medium contained in oxidation zone 110.

In one embodiment of the present invention, oxidation zone 110 can comprise an agitated reactor. Agitation of the reaction medium in oxidation zone 110 can be provided by any means known in the art. As used herein, the term "agitation" shall denote work dissipated into the reaction medium causing fluid flow and/or mixing. In one embodiment, oxidation zone 110 can be a mechanically-agitated reactor equipped with means for mechanically agitating the reaction medium. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. In another embodiment of the present invention, oxidation zone 110 can comprise a bubble column reactor. As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the terms "majority," "primarily," and "predominately" shall mean more than 50 percent.

The oxidizable compound present in the fluid-phase feed stream introduced into oxidation zone 110 can comprise at least one hydrocarbyl group. Also, the oxidizable compound can comprise an aromatic compound. In one embodiment, the oxidizable compound can comprise an aromatic compound with at least one attached hydrocarbyl group or at least one attached substituted hydrocarbyl group or at least one attached heteroatom or at least one attached carboxylic acid function (—COOH). In another embodiment, the oxidizable compound can comprise an aromatic compound with at least one attached hydrocarbyl group or at least one attached substituted hydrocarbyl group with each attached group comprising from 1 to 5 carbon atoms. In yet another embodiment, the oxidizable compound can be an aromatic compound having exactly two attached groups with each attached group comprising exactly one carbon atom and consisting of methyl groups and/or substituted methyl groups and/or at most one carboxylic acid group. Suitable examples of the oxidizable compound include, but are not limited to, para-xylene, meta-xylene, para-tolualdehyde, meta-tolualdehyde, para-toluic acid, and/or meta-toluic acid. In one embodiment of the present invention, the oxidizable compound comprises para-xylene.

A "hydrocarbyl group," as defined herein, is at least one carbon atom that is bonded only to hydrogen atoms and/or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. "Aromatic compounds," as defined herein, comprise an aromatic ring and can comprise at least 6 carbon atoms and can also comprise only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the fluid-phase feed stream introduced into oxidation zone 110 can be in the range of from about 4 to about 20 weight percent, or in the range of from 6 to 15 weight percent.

The solvent present in the fluid-phase feed stream introduced into oxidation zone 110 can comprise an acid component and a water component. The solvent can be present in the fluid-phase feed stream at a concentration in the range of from about 60 to about 98 weight percent, in the range of from about 80 to about 96 weight percent, or in the range of from 85 to 94 weight percent. The acid component of the solvent can be an organic low molecular weight monocarboxylic acid having from 1 to 6 carbon atoms, or 2 carbon atoms. In one embodiment, the acid component of the solvent can comprise acetic acid. The acid component can make up at least about 75 weight percent of the solvent, at least about 80 weight percent of the solvent, or in the range of from 85 to 98 weight percent of the solvent, with the balance being water.

As mentioned above, the fluid-phase feed stream introduced into oxidation zone 110 can also include a catalyst system. The catalyst system can be a homogeneous, liquid-phase catalyst system capable of promoting at least partial oxidation of the oxidizable compound. Also, the catalyst system can comprise at least one multivalent transition metal. In one embodiment, the catalyst system can comprise cobalt, bromine, and/or manganese.

When cobalt is present in the catalyst system, the fluid-phase feed stream can comprise cobalt in an amount such that the concentration of cobalt in the liquid phase of the reaction medium is maintained in the range of from about 300 to about 6,000 parts per million by weight (ppmw), in the range of from about 700 to about 4,200 ppmw, or in the range of from 1,200 to 3,000 ppmw. When bromine is present in the catalyst system, the fluid-phase feed stream can comprise bromine in an amount such that the concentration of bromine in the liquid phase of the reaction medium is maintained in the range of from about 300 to about 5,000 ppmw, in the range of from about 600 to about 4,000 ppmw, or in the range of from 900 to 3,000 ppmw. When manganese is present in the catalyst system, the fluid-phase feed stream can comprise manganese in an amount such that the concentration of manganese in the liquid phase of the reaction medium is maintained in the range of from about 20 to about 1,000 ppmw, in the range of from about 40 to about 500 ppmw, or in the range of from 50 to 200 ppmw.

In one embodiment of the present invention, cobalt and bromine can both be present in the catalyst system. The weight ratio of cobalt to bromine (Co:Br) in the catalyst system can be in the range of from about 0.25:1 to about 4:1, in the range of from about 0.5:1 to about 3:1, or in the range of from 0.75:1 to 2:1. In another embodiment, cobalt and manganese can both be present in the catalyst system. The weight ratio of cobalt to manganese (Co:Mn) in the catalyst system can be in the range of from about 0.3:1 to about 40:1, in the range of from about 5:1 to about 30:1, or in the range of from 10:1 to 25:1.

During oxidation, the oxidizable compound (e.g., para-xylene) can be continuously introduced into oxidation zone 110 at a rate of at least about 5,000 kilograms per hour, at a rate in the range of from about 10,000 to about 80,000 kilograms per hour, or in the range of from 20,000 to 50,000 kilograms per hour. During oxidation, the ratio of the mass flow rate of the solvent to the mass flow rate of the oxidizable compound entering oxidation zone 110 can be maintained in the range of from about 2:1 to about 50:1, in the range of from about 5:1 to about 40:1, or in the range of from 7.5:1 to 25:1.

The predominately gas-phase oxidant stream introduced into oxidation zone 110 can comprise in the range of from about 5 to about 40 mole percent molecular oxygen, in the range of from about 15 to about 30 mole percent molecular oxygen, or in the range of from 18 to 24 mole percent molecular oxygen. The balance of the oxidant stream can be comprised primarily of a gas or gases, such as nitrogen, that are inert to oxidation. In one embodiment, the oxidant stream consists essentially of molecular oxygen and nitrogen. In another embodiment, the oxidant stream can be dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in oxidation zone 110, the oxidant stream can be introduced into oxidation zone 110 in an amount that provides molecular oxygen somewhat exceeding the stoichiometric oxygen demand. Thus, the ratio of the mass flow rate of the oxidant stream (e.g., air) to the mass flow rate of the oxidizable compound (e.g., para-xylene) entering oxidation zone 110 can be maintained in the range of from about 0.5:1 to about 20:1, in the range of from about 1:1 to about 10:1, or in the range of from 2:1 to 6:1.

The liquid-phase oxidation reaction carried out in oxidation zone 110 can be a precipitating reaction that generates solids. In one embodiment, the liquid-phase oxidation carried out in oxidation zone 110 can cause at least about 10 weight percent of the oxidizable compound (e.g., para-xylene) introduced into oxidation zone 110 to form solids (e.g., crude terephthalic acid (CTA) particles) in the reaction medium. In another embodiment, the liquid-phase oxidation carried out in oxidation zone 110 can cause at least about 50 weight percent of the oxidizable compound (e.g., para-xylene) introduced into oxidation zone 110 to form solids (e.g., CTA particles) in the reaction medium. In yet another embodiment, the liquid-phase oxidation carried out in oxidation zone 110 can cause at least about 90 weight percent of the oxidizable compound (e.g., para-xylene) introduced into oxidation zone 110 to form solids (e.g., CTA particles) in the reaction medium. In one embodiment, the solids content of the reaction medium can be maintained in the range of from about 1 to about 50 weight percent, in the range of from about 5 to about 40 weight percent, in the range of from about 10 to about 35 weight percent, or in the range of from 15 to 30 weight percent. As used herein, the term "solids content" shall denote the weight percent solids in a multi-phase mixture.

During oxidation in oxidation zone 110, the multi-phase reaction medium can be maintained at an elevated temperature in the range of from about 125 to about 200° C., in the range of from about 150 to about 180° C., or in the range of from 155 to 165° C. The overhead pressure in oxidation zone, 110 can be maintained in the range of from about 1 to about 20 bar gauge (barg), in the range of from about 2 to about 12 barg, or in the range of from 4 to 8 barg.

In the embodiment of FIG. 2, a crude slurry can be withdrawn from an outlet of oxidation zone 110 via line 112. The solid phase of the crude slurry in line 112 can be formed primarily of CTA particles. The liquid phase of the crude slurry in line 112 can be a liquid mother liquor comprising at least a portion of the solvent, one or more catalyst components, and minor amounts of dissolved terephthalic acid (TPA). In one embodiment, the crude slurry in line 112 can comprise acetic acid in an amount of at least about 10 weight percent. The solids content of the crude slurry in line 112 can be the same as the solids content of the reaction medium in oxidation zone 110, discussed above. In another embodiment, the crude slurry in line 112 can have a solids content of at least about 15 weight percent.

In one embodiment of the present invention, the crude slurry in line 112 can comprise impurities. As used herein, the term "impurities" is defined as any substance other than TPA, solvent, catalyst, and water. Such impurities can include oxidation byproducts formed during the at least partial oxidation of the above-mentioned oxidizable compound (e.g., para-xylene) including, but not limited to, benzoic acid (BA), bromo-benzoic acid, bromo-acetic acid, isophthalic acid, trimellitic acid, 2,5,4'-tricarboxybiphenyl, 2,5,4'-tricarboxybenzophenone, para-toluic acid (p-TAc), 4-carboxybenzaldehyde (4-CBA), monocarboxyfluorenones, monocarboxyfluorenes, dicarboxyfluorenes, and/or dicarboxyfluorenones.

Subsequent to removal from oxidation zone 110, at least a portion of the crude slurry (i.e., the purification feed slurry) can be introduced into purification zone 114 via line 112. In one embodiment, the crude slurry can be treated in purification zone 114 such that the concentration of at least one of the above-mentioned impurities in the crude slurry is reduced, thereby producing a purified slurry. Such reduction in the concentration of impurities in the TPA can be accomplished by oxidative digestion, hydrogenation, and/or dissolution/recrystallization.

In one embodiment of the present invention, the crude slurry fed to purification zone 114 can have a 4-CBA content of at least about 100 parts per million based on the weight of the solids in the crude slurry ($ppmw_{cs}$), in the range of from about 200 to about 10,000 $ppmw_{cs}$, or in the range of from 800 to 5,000 $ppmw_{cs}$. The crude slurry fed to purification zone 114 can have a p-TAc content of at least about 250 $ppmw_{cs}$, in the range of from about 300 to about 5,000 $ppmw_{cs}$, or in the range of from 400 to 1,500 $ppmw_{cs}$. The purified slurry exiting purification zone 114 can have a 4-CBA content of less than about 150 parts per million based on the weight of the solids in the purified slurry ($ppmw_{ps}$), less than about 100 $ppmw_{ps}$, or less than 50 $ppmw_{ps}$. The purified slurry exiting purification zone 114 can have a p-TAc content of less than about 300 $ppmw_{ps}$, less than about 200 $ppmw_{ps}$, or less than 150 $ppmw_{ps}$. In one embodiment, treatment of the crude slurry in purification zone 114 can cause the purified slurry exiting purification zone 114 to have a 4-CBA and/or p-TAc content that is at least about 50 percent less than the 4-CBA and/or p-TAc content of the crude slurry fed to purification zone 114, at least about 85 percent less, or at least 95 percent less. By way of illustration, if the 4-CBA content of the crude slurry fed to purification zone 114 is 200 $ppmw_{cs}$ and the 4-CBA content of the purified slurry exiting purification zone 114 is 100 $ppmw_{ps}$, then the 4-CBA content of the purified slurry is 50 percent less than the 4-CBA content of the crude slurry.

In one embodiment of the present invention, the crude slurry can be subjected to purification by oxidative digestion in purification zone 114. As used herein, the term "oxidative digestion" denotes a process step or steps where a feed comprising solid particles is subjected to oxidation under conditions sufficient to permit oxidation of at least a portion of the impurities originally trapped in the solid particles. Purification zone 114 can comprise one or more reactors or zones. In one embodiment, purification zone 114 can comprise one or more mechanically-agitated reactors. A secondary oxidant stream, which can have the same composition as the gas-phase oxidant stream fed to oxidation zone 110, can be introduced into purification zone 114 to provide the molecular oxygen required for oxidative digestion. Additional oxidation catalyst can be added if necessary. In an alternative embodiment of the present invention, a stream comprising hydrogen can be introduced into purification zone 114 for at least partial hydrogenation of the crude slurry.

When oxidative digestion is employed in purification zone 114, the temperature at which oxidative digestion is carried out can be at least about 10° C. greater than the temperature of oxidation in oxidation zone 110, in the range of from about 20 to about 80° C. greater, or in the range of from 30 to 50° C. greater. The additional heat required for the operation of purification zone 114 can be provided by supplying a vaporized solvent to purification zone 114 and allowing the vaporized solvent to condense therein. The oxidative digestion temperature in purification zone 114 can be maintained in the range of from about 180 to about 240° C., in the range of from about 190 to about 220° C., or in the range of from 200 to 210° C. The oxidative digestion pressure in purification zone 114 can be maintained in the range of from about 100 to about 350 pounds per square inch gauge (psig), in the range of from about 175 to about 275 psig, or in the range of from 185 to 225 psig.

In one embodiment of the present invention, purification zone 114 can include two digestion reactors/zones—an initial digester and a final digester. When purification zone 114 includes an initial digester and a final digester, the final digester can be operated at a lower temperature and pressure than the initial digester. In one embodiment, the operating temperature of the final digester can be at least about 2° C. lower than the operating temperature of the initial digester, or in the range of from about 5 to about 15° C. lower than the operating temperature of the initial digester. In one embodiment, the operating pressure of the final digester can be at least about 5 psig lower than the operating pressure of the initial digester, or in the range of from about 10 to about 50 psig lower than the operating pressure of the initial digester. The operating temperature of the initial digester can be in the range of from about 195 to about 225° C., in the range of from 205 to 215° C., or about 210° C. The operating pressure of the initial digester can be in the range of from about 215 to about 235 psig, or about 225 psig. The operating temperature of the final digester can be in the range of from about 190 to about 220° C., in the range of from 200 to 210° C., or about 205° C. The operating pressure of the final digester can be in the range of from about 190 to 210 psig, or about 200 psig.

In one embodiment of the present invention, purification zone 114 can comprise optional first and second solvent swap zones. Optional first and second solvent swap zones can operate to replace at least a portion of the existing solvent in a slurry with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with optional counter current washing. The replacement oxidation solvent can have substantially the same composition as the solvent introduced into oxidation zone 110, as described above.

In one embodiment, the crude slurry fed to purification zone 114 can be treated in the optional first solvent swap zone prior to purification of the crude slurry by the above-mentioned oxidative digestion. In another embodiment, a purified slurry resulting from oxidative digestion of the crude slurry can be treated in the optional second solvent swap zone.

Optionally, at least a portion of the displaced oxidation solvent from the optional first and/or second solvent swap zones can be discharged from purification zone 114 via line 138. At least a portion of the displaced oxidation solvent in line 138 can be routed to solids removal zone 132 via line 140, purge treatment zone 162 via line 138a, and/or oxidation zone 110 via line 138b.

In another embodiment of the present invention, purification zone 114 can comprise an optional crystallization zone and/or an optional cooling zone. A purified slurry resulting from the above-mentioned oxidative digestion of the crude slurry can be treated in the optional crystallization zone to at least partially increase the particle size distribution of the purified slurry. Optional crystallization zone can comprise any equipment known in the art that can operate to increase the particle size distribution of the purified slurry. When an optional cooling zone is employed, the purified slurry can be cooled therein to a temperature in the range of from about 20 to about 195° C. When both a crystallization zone and a cooling zone are employed, the purified slurry can be treated first in the crystallization zone and subsequently in the cooling zone.

Referring still to FIG. 2, a purified slurry can be withdrawn from an outlet of purification zone 114 via line 40. The solid phase of the purified slurry can be formed primarily of purified terephthalic acid (PTA) particles, while the liquid phase can be formed of a mother liquor. The solids content of the purified slurry in line 40 can be in the range of from about 1 to about 50 percent by weight, in the range of from about 5 to about 40 weight percent, or in the range of from 20 to 35 weight percent. In one embodiment of the present invention, at least a portion of the purified slurry in line 40 can be employed as an isolation feed slurry which can be introduced into product isolation zone 100. In the embodiment of FIG. 2, product isolation zone 100 can operate in substantially the same manner as discussed above with reference to FIG. 1.

As discussed above with reference to FIG. 1, product isolation zone 100 can separate the isolation feed slurry into a primarily fluid phase mother liquor and a primarily solid phase product wet cake comprising isolated solids. The wet cake generated in product isolation zone 100 can be discharged via line 52. In one embodiment of the present invention, the wet cake generated in product isolation zone 100 can primarily comprise solid particles of TPA. The solid TPA particles can comprise PTA particles. The wet cake can comprise in the range of from about 5 to about 30 weight percent liquid, in the range of from about 10 to about 25 weight percent liquid, or in the range of from 12 to 23 weight percent liquid. Additionally, the product wet cake in line 52 can comprise oxidation byproducts, such as those discussed above.

Referring still to FIG. 2, in one embodiment, at least a portion of the wet cake in line 52 can be introduced into drying zone 122 to thereby produce a dried TPA particulate product comprising solid TPA particles. Drying zone 122 can comprise any drying device known in the art that can produce a dried TPA particulate product comprising less than about 5 weight percent liquid, less than about 3 weight percent liquid, or less than 1 weight percent liquid. Dried TPA particulate product can be discharged from drying zone 122 via line 124.

In another embodiment, at least a portion of the wet cake in line 52 can be introduced into solvent swap zone 126 to thereby produce a wet TPA particulate product comprising solid TPA particles. Solvent swap zone 126 can operate to replace at least a portion of the liquid in the wet cake with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with counter current washing. Wet TPA particulate product can be discharged from solvent swap zone 126 via line 128. The wet TPA particulate product can comprise in the range of from about 5 to about 30 weight percent liquid, in the range of from about 10 to about 25 weight percent liquid, or in the range of from 12 to 23 weight percent liquid.

Referring still to FIG. 2, the above-mentioned mother liquor can be discharged from product isolation zone 100 via line 44. In one embodiment of the present invention, at least a portion of the mother liquor in line 44 can optionally be introduced into solids removal zone 132. Solids removal zone 132 can comprise any equipment known in the art that is operable to remove a sufficient amount of solids from the mother liquor to produce a solids-depleted mother liquor comprising less than about 5 weight percent solids, less than about 2 weight percent solids, or less than 1 weight percent solids. Suitable equipment that may be employed in solids removal zone 132 includes a pressure filter, such as, for example, a filter press, a candle filter, a pressure leaf filter, and/or a cartridge filter. In one embodiment, solids removal zone 132 can be operated at a temperature in the range of from about 20 to about 195° C. and a pressure in the range of from about 750 to about 3,750 torr during solids removal. The solids-depleted mother liquor can be discharged from solids removal zone 132 via line 134. In one embodiment of the present invention, at least a portion of the solids removed from the mother liquor in solids removal zone 132 can be discharged via line 136 and can be routed to product isolation zone 100 via line 136a and/or to line 52 via line 136b.

As mentioned above, at least a portion of the displaced oxidation solvent from purification zone 114 can also optionally be treated in solids removal zone 132. Such displaced oxidation solvent can be withdrawn from purification zone 114 via line 138 and introduced into solids removal zone 132 via line 140. When displaced oxidation solvent from oxidation zone 114 is treated in solids removal zone 132, the resulting solids-depleted displaced oxidation solvent can be combined with the solids-depleted mother liquor and can be discharged via line 134.

In one embodiment of the present invention, at least a portion of the optionally solids-depleted mother liquor in line 134 can be withdrawn from line 134 via line 142 to form a purge feed stream. The amount of mother liquor withdrawn by line 142 to form the purge feed stream can be in the range of from about 1 to about 55 percent of the total weight of the mother liquor, in the range of from about 5 to about 45 percent by weight, or in the range of from 10 to 35 percent by weight. Optionally, at least a portion of the displaced oxidation solvent discharged from purification zone 114 in line 138 can be combined with the purge feed stream via line 138a. In another embodiment, at least a portion of the remaining mother liquor in line 134 can be routed, either directly or indirectly, to oxidation zone 110 via line 144. Optionally, at least a portion of the wash liquor discharged from product isolation zone 100 can be combined with at least a portion of the mother liquor in line 144 prior to introduction into oxidation zone 110.

In one embodiment of the present invention, the mother liquor in line 134, and consequently the purge feed stream in line 142, can comprise solvent, one or more catalyst components, oxidation byproducts, and TPA. The solvent in the mother liquor in line 134 and the purge feed stream in line 142 can comprise a monocarboxylic acid. In one embodiment, the solvent can comprise water and/or acetic acid. The mother liquor in line 134 and the purge feed stream in line 142 can comprise solvent in an amount of at least about 85 weight percent, at least about 95 weight percent, or at least 99 weight percent.

The catalyst components in the mother liquor in line 134 and the purge feed stream in line 142 can comprise the catalyst components as described above with reference to the catalyst system introduced into oxidation zone 110 (e.g., cobalt, manganese, and/or bromine). The mother liquor in line 134 and the purge feed stream in line 142 can have a cumulative concentration of all of the catalyst components in the range of from about 500 to about 20,000 ppmw, in the range of from about 1,000 to about 15,000 ppmw, or in the range of from 1,500 to 10,000 ppmw.

The oxidation byproducts in the mother liquor in line 134 and the purge feed stream in line 142 can comprise one or more of the oxidation byproducts discussed above. In one embodiment, the oxidation byproducts in the mother liquor in line 134 and the purge feed stream in line 142 can comprise both BA and non-BA byproducts. As used herein, the term "non-BA byproducts" is defined as any oxidation byproduct that is not benzoic acid. Non-BA byproducts include, but are not limited to, isophthalic acid (IPA), phthalic acid (PA), trimellitic acid, 2,5,4'-tricarboxybiphenyl, 2,5,4'-tricarboxybenzophenone, p-TAc, 4-CBA, naphthalene dicarboxylic acid, monocarboxyfluorenones, monocarboxyfluorenes, dicarboxyfluorenes, and/or dicarboxyfluorenones. In one embodiment, the mother liquor in line 134 and the purge feed stream in line 142 can comprise BA in an amount in the range of from about 500 to about 150,000 ppmw based on the weight of the purge feed stream, in the range of from about 1,000 to about 100,000 ppmw, or in the range of from 2,000 to 50,000 ppmw. Additionally, the mother liquor in line 134 and the purge feed stream in line 142 can have a cumulative concentration of non-BA byproducts in the range of from about 500 to about 50,000 ppmw, in the range of from about 1,000 to about 20,000 ppmw, or in the range of from 2,000 to 10,000 ppmw.

In one embodiment of the present invention, the mother liquor in line 134 and the purge feed stream in line 142 can comprise solids in an amount of less than about 5 weight percent, less than about 2 weight percent, or less than 1 weight percent. Additionally, the purge feed stream can have a temperature of less than about 240° C., in the range of from about 20 to about 200° C., or in the range of from 50 to 100° C.

Referring still to FIG. 2, the purge feed stream can be introduced into purge treatment zone 162 via line 142. Purge treatment zone 162 can separate the purge feed stream into a catalyst rich stream, a BA rich stream, and a non-BA byproduct rich stream. The BA rich stream can be discharged from purge treatment zone 162 via line 148, the catalyst rich stream can be discharged from purge treatment zone 162 via line 150, and the non-BA byproduct rich stream can be discharged from purge treatment zone 162 via line 152.

The BA rich stream in line 148 can have a relatively higher concentration of BA on a weight basis compared to the BA concentration of the purge feed stream in line 142. In one embodiment of the present invention, the BA rich stream in line 148 can have a concentration of BA that is at least about 1.5 times the concentration of BA in the purge feed stream on a weight basis, at least about 5 times the concentration of BA in the purge feed stream on a weight basis, or at least 10 times the concentration of BA in the purge feed stream on a weight basis. In one embodiment, BA can be the primary oxidation byproduct in the BA rich stream. Depending of the temperature and pressure of the BA rich stream upon exiting purge treatment zone 162, the BA rich stream in line 148 can predominately comprise solids or fluid. Thus, in one embodiment, the BA rich stream in line 148 can comprise at least about 50 weight percent fluid, at least about 70 weight percent fluid, or at least about 90 weight percent fluid. In an alternate embodiment, the BA rich stream in line 148 can comprise at least about 50 weight percent solids, at least about 70 weight percent solids, or at least 90 weight percent solids.

The catalyst rich stream in line 150 can have a relatively higher cumulative concentration of all of the catalyst components on a weight basis compared to the cumulative concentration of all of the catalyst components in the purge feed stream in line 142. In one embodiment of the present invention, the catalyst rich stream in line 150 can have a cumulative concentration of all of the catalyst components that is at least about 1.5 times the cumulative concentration of all of the catalyst components in the purge feed stream on a weight basis, at least about 5 times the cumulative concentration of all of the catalyst components in the purge feed stream on a weight basis, or at least 10 times the cumulative concentration of all of the catalyst components in the purge feed stream on a weight basis. Depending of the temperature and pressure of the catalyst rich stream upon exiting purge treatment zone 162, the catalyst rich stream in line 150 can predominately comprise solids or fluid. Thus, in one embodiment, the catalyst rich stream in line 150 can comprise at least about 50 weight percent fluid, at least about 70 weight percent fluid, or at least 90 weight percent fluid. In an alternate embodiment, the catalyst rich stream in line 150 can comprise at least about 50 weight percent solids, at least about 70 weight percent solids, or at least 90 weight percent solids.

The non-BA byproduct rich stream in line 152 can have a relatively higher cumulative concentration of non-BA byproducts on a weight basis compared to the cumulative concentration of non-BA byproducts in the purge feed stream in line 142. In one embodiment of the present invention, the non-BA byproduct rich stream in line 152 can have a cumulative concentration of non-BA byproducts that is at least about 1.5 times the cumulative concentration of non-BA byproducts in the purge feed stream on a weight basis, at least about 5 times the cumulative concentration of non-BA byproducts in the purge feed stream on a weight basis, or at least 10 times the cumulative concentration of non-BA byproducts in the purge feed stream on a weight basis. In one embodiment, non-BA byproducts can cumulatively be the primary oxidation byproducts in the non-BA byproduct rich stream. The non-BA byproduct rich stream in line 152 can be in the form of a wet cake, comprising in the range of from about 5 to about 30 weight percent liquid, in the range of from 10 to about 25 weight percent liquid, or in the range of from 12 to 23 weight percent liquid.

In one embodiment of the present invention, at least a portion of the BA rich stream, the catalyst rich stream, and the non-BA byproduct rich stream can be routed to different locations. Such locations include, but are not limited to, various points in a TPA production process, an IPA production process, a phthalic acid (PA) production process, a BA production process, a naphthalene-dicarboxylic acid (NDA) production process, a dimethylterephthalate (DMT) production process, a dimethylnaphthalate (DMN) production process, a cyclohexane dimethanol (CHDM) production process, a dimethyl-cyclohexanedicarboxylate (DMCD) production process, a cyclohexanedicarboxylic acid (CHDA) production process, a polyethylene terephthalate (PET) production process, a production process for any isomers of NDA, DMT, DMN, CHDM, DMCD, CHDA, a copolyester production process, a polymer production process employing one or more of TPA, IPA, PA, BA, NDA, DMT, DMN, CHDM, DMCD, CHDA, or any isomers thereof as one component and/or as a monomer, and/or outside the TPA, IPA, PA, BA, NDA, DMT, DMN, CHDM, DMCD, CHDA, PET, or polymer production processes.

In one embodiment, the amount of BA that exits the TPA production process with the TPA product (i.e., the isolated product) and/or is combined with the TPA product downstream of the TPA production process can be sufficient to result in a TPA product comprising BA in an amount of less than about 1,000 ppmw, less than about 500 ppmw, or less than 250 ppmw. In another embodiment, the rate at which BA exits the TPA production process with the TPA product and/or is combined with the TPA product downstream of the TPA production process can be less than about 50 percent, less than about 10 percent, less than about 1 percent, or less than 0.1 percent of the make rate of BA in the TPA production process. As used herein with reference to BA, the term "make rate" is defined as the difference between the mass per unit time of BA entering the oxidation step (e.g., oxidation zone 110) and the mass per unit time of BA exiting the purification step (e.g., purification zone 114). By way of illustration, if BA enters the oxidation step of the TPA production process at a rate of 50 kilograms per hour (kg/hr), and BA exits the purification step at a rate of 150 kg/hr, then the make rate of BA in the TPA production process is 100 kg/hr.

In another embodiment, at least a portion of the BA rich stream can exit the process depicted in FIG. 2 and be routed to a purification and recovery process, a subsequent chemical process, and/or a waste treatment or disposal process. Such waste treatment or disposal processes include, but are not limited to, sale, burial, incineration, neutralization, anaerobic and/or aerobic digestion, treatment in a waste oxidizer, and/or treatment in a waste reactor. In one embodiment of the present invention, at least a portion of the BA rich stream can be routed to a waste treatment process where at least about 50 weight percent, at least about 60 weight percent, or at least 70 weight percent of the BA present in the BA rich stream is treated.

As mentioned above, the catalyst rich stream in line 150 can be routed to various points in a TPA production process. In one embodiment of the present invention, at least a portion of the catalyst rich stream in line 150 can be routed, either directly or indirectly, to oxidation zone 110, where at least about 50 weight percent, at least about 60 weight percent, or at least 70 weight percent of the catalyst components of the catalyst rich stream are introduced into oxidization zone 110. In one embodiment, prior to routing, a liquid can optionally be added to the catalyst rich stream in line 150 to produce a reslurried catalyst rich stream. The reslurried catalyst rich stream can comprise at least about 35 weight percent liquid, at least about 50 weight percent liquid, or at least 65 weight percent liquid. The liquid added to the catalyst rich stream can be, for example, acetic acid and/or water.

Referring still to FIG. 2, as noted above, the non-BA byproduct rich stream in line 152 can be routed to various points in the depicted TPA production process. Such routing includes, but is not limited to, returning at least a portion of the non-BA byproduct rich stream, either directly or indirectly, to oxidation zone 110 and/or purification zone 114. In one embodiment, at least a portion of the non-BA byproduct rich stream can be routed such that at least a portion of the non-BA byproducts in the non-BA byproduct rich stream exit the TPA production process with the dried TPA product discharged from line 124 and/or with the wet TPA product discharged from line 128. For example, at least a portion of the non-BA byproduct rich stream can be introduced into the purified slurry in line 40 and/or into the isolated product in line 52 and allowed to exit the TPA production process with the TPA product. In another embodiment, at least a portion of the non-BA byproducts in the non-BA byproduct rich stream can be combined with the TPA product downstream of the TPA production process. In one embodiment, at least about 5 weight percent, at least about 25 weight percent, at least about 50 weight percent, or at least 75 weight percent of the non-BA byproducts in the non-BA byproduct rich stream can be allowed to exit the TPA production process with the TPA product and/or can be combined with the TPA product downstream of the TPA production process.

In one embodiment, the cumulative rate at which the non-BA byproducts exit the TPA production process with the TPA product and/or are combined with the TPA product downstream of the TPA production process can be at least about 5 percent, at least about 10 percent, at least about 20 percent, or at least 50 percent of the make rate of the non-BA byproducts in the TPA production process. As used herein with reference to non-BA byproducts, the term "make rate" is defined as the difference between the mass per unit time of non-BA byproducts entering the oxidation step (e.g., oxidation zone 110) and the mass per unit time of non-BA byproducts exiting the purification step (e.g., purification zone 114). By way of illustration, if non-BA byproducts enter the oxidation step of the TPA production process at a rate of 50 kg/hr, and non-BA byproducts exit the purification step at a rate of 150 kg/hr, then the make rate of non-BA byproducts in the TPA production process is 100 kg/hr.

In another embodiment, the non-BA byproduct rich stream can exit the process depicted in FIG. 2 and can be routed to a purification and recovery process, a process utilizing non-BA byproducts for making non-BA byproduct derivatives, and/or a waste treatment or disposal process. Such waste treatment or disposal processes include, but are not limited to, sale, burial, incineration, neutralization, anaerobic and/or aerobic digestion, treatment in a waste oxidizer, and/or treatment in a waste reactor.

As mentioned above, the non-BA byproduct rich stream in line 152 can be in the form of a wet cake. In one embodiment of the present invention, prior to routing the non-BA byproduct rich stream, at least a portion the non-BA byproduct rich stream may optionally be dried in drying zone 154. Drying zone 154 can comprise any drying device known in the art that can produce a dried non-BA byproduct rich stream comprising less than about 5 weight percent liquid, less than about 3 weight percent liquid, or less than 1 weight percent liquid. The optionally dried non-BA byproduct rich stream can be discharged from drying zone 154 via line 156.

In another embodiment, prior to routing the non-BA byproduct rich stream, a liquid may be added to at least a portion of the non-BA byproduct rich stream in reslurry zone 158 to produce a reslurried non-BA byproduct rich stream. The reslurried non-BA byproduct rich stream can be discharged from reslurry zone 158 via line 160. The reslurried non-BA byproduct rich stream can comprise at least about 35 weight percent liquid, at least about 50 weight percent liquid, or at least 65 weight percent liquid. The liquid added to the non-BA byproduct rich stream in reslurry zone 158 can comprise acetic acid and/or water.

FIG. 3 illustrates another embodiment of the present invention where the product isolation device discussed above with reference to FIG. 1 can be employed in a carboxylic acid production process where carboxylic acid produced in an oxidation reactor and purified in a purification reactor is subjected to product isolation in product isolation zone 100. As discussed above, product isolation zone 100 can separate the isolation feed slurry in line 40 into a mother liquor and an isolated product. In the embodiment of FIG. 3, at least a portion of the mother liquor generated in product isolation zone 100 can be treated in a concentration zone and resolved into a catalyst and byproduct rich stream and a solvent rich stream.

In the embodiment illustrated in FIG. 3, oxidation zone 110 and purification zone 114 can be operated in substantially the same manner as discussed above with reference to FIG. 2 to produce a purified slurry. In one embodiment, at least a portion of the purified slurry in line 40 can be employed as an isolation feed slurry which can be introduced into product isolation zone 100.

As discussed above with reference to FIG. 1, product isolation zone 100 can separate the isolation feed slurry into a primarily fluid phase mother liquor and a primarily solid phase isolated product wet cake comprising isolated solids. The isolated solids generated in product isolation zone 100 can be discharged via line 52. In the embodiment of FIG. 3, the isolated solids can comprise purified solids comprising purified carboxylic acid (e.g., PTA). The isolated solids can also comprise oxidation byproducts. The types of oxidation byproducts in the isolated solids can be the same as the oxidation byproducts discussed above in relation to the crude slurry in line 112, discussed above with reference to FIG. 2. In the embodiment of FIG. 3, the individual solid particles that make up the isolated solids can comprise concentrations of carboxylic acid and oxidation byproducts in any ratio. In other words, an individual solid particle in the isolated solids can be comprised completely of oxidation byproducts, completely of carboxylic acid, or any possible combination of carboxylic acid and oxidation byproducts.

In the embodiment of FIG. 3, the rate at which oxidation byproducts exit product isolation zone 100 with the isolated solids can be at least about 15 percent, at least about 40 percent, at least about 60 percent, at least about 80 percent, or at least 90 percent of the net make rate of the oxidation byproducts in the carboxylic acid production process. As used herein, the term "net make rate" is defined as the difference between the mass per unit time of oxidation byproducts entering the oxidation step (e.g., oxidation zone 110) and the mass per unit time of oxidation byproducts exiting the purification step (e.g., purification zone 114) minus the mass per unit time of any additional step (e.g., BA oxidizer 308, discussed in greater detail below) in the carboxylic acid production process that results in the destruction and/or conversion of any oxidation byproducts. By way of illustration, if oxidation byproducts enter the oxidation step of the production process at a rate of 50 kilograms per hour (kg/hr), oxidation byproducts exit the purification step at a rate of 150 kg/hr, and oxidation byproducts are destroyed and/or converted in an additional step at a rate of 25 kg/hr, then the net make rate of oxidation byproducts in the production process is 75 kg/hr. In one embodiment of the present invention, the net make rate of oxidation byproducts in the carboxylic acid production process can be at least about 5 kg/hr, in the range of from about 5 to about 20,000 kg/hr, in the range of from about 10 to about 10,000 kg/hr, or in the range of from 20 to 5,000 kg/hr.

In another embodiment, oxidation byproducts can additionally be combined with the isolated solids downstream of product isolation zone 100, such that the rate at which oxidation byproducts exit product isolation zone 100 with the isolated solids and/or are combined with the isolated solids downstream of product isolation zone 100 is at least about 15 percent, at least about 40 percent, at least about 60 percent, at least about 80 percent, or at least 90 percent of the net make rate of the oxidation byproducts in the carboxylic acid production process. In another embodiment, all of the oxidation byproducts generated in the production process can exit the carboxylic acid production process with the isolated product at rates at or near their respective make rates in the process. In another embodiment, substantially all of the oxidation byproducts that enter product isolation zone 100 can exit product isolation zone 100 with the isolated solids and/or can be returned, either directly or indirectly, to a point in the production process upstream of product isolation zone 100.

The above-mentioned isolated product can comprise a concentration of oxidation byproducts of at least about 500 ppmw. In another embodiment, the isolated product can comprise a concentration of oxidation byproducts in the range of from about 1,000 to about 100,000 ppmw, in the range of from about 3,000 to about 75,000 ppmw, or in the range of from 5,000 to 50,000 ppmw.

Referring still to FIG. 3, the above-mentioned mother liquor can be discharged from product isolation zone 100 via line 44. In one embodiment of the present invention, at least a portion of the mother liquor in line 44 can be withdrawn via line 234 to form a purified concentration feed stream, which can be fed to concentration zone 236. The amount of mother liquor withdrawn by line 234 to form the purified concentration feed stream can be in the range of from about 1 to about 55 percent of the total weight of the mother liquor, in the range of from about 5 to about 45 percent by weight, or in the range of from 10 to 35 percent by weight. At least a portion of the displaced oxidation solvent discharged from purification zone 114 in line 138 can be introduced into concentration zone 236 via line 138a. Alternatively, the displaced oxidation solvent in line 138a can be combined with the purified concentration feed stream in line 234 prior to being introduced into concentration zone 236.

In another embodiment, at least a portion of the remaining mother liquor in line 44 can be routed, either directly or indirectly, to oxidation zone 110 via line 240. Optionally, at least a portion of the wash liquor in line 46 can be combined with at least a portion of the mother liquor in line 240 prior to introduction into oxidation zone 110.

In one embodiment of the present invention, the mother liquor in line 44, and consequently the purified concentration feed in line 234, can comprise solvent, one or more catalyst components, oxidation byproducts, and TPA. The solvent in the mother liquor in line 44 and the purified concentration feed in line 234 can comprise a monocarboxylic acid. In one embodiment, the solvent can comprise water and/or acetic acid. The mother liquor in line 44 and the purified concentration feed stream in line 234 can comprise solvent in an amount of at least about 85 weight percent, at least about 95 weight percent, or at least 99 weight percent.

The catalyst components in the mother liquor in line 44 and the purified concentration feed stream in line 234 can comprise the catalyst components as described above with reference to the catalyst system introduced into oxidation zone 110 (e.g., cobalt, manganese, and/or bromine). The mother liquor in line 44 and the purified concentration feed stream in line 234 can have a cumulative concentration of all of the catalyst components in the range of from about 500 to about 20,000 ppmw, in the range of from about 1,000 to about 15,000 ppmw, or in the range of from 1,500 to 10,000 ppmw.

The oxidation byproducts in the mother liquor in line 44 and the purified concentration feed stream in line 234 can comprise one or more of the oxidation byproducts discussed above. In one embodiment, the mother liquor in line 44 and the purified concentration feed stream in line 234 can have a cumulative concentration of all of the oxidation byproducts in the range of from about 1,000 to about 200,000 ppmw based on the weight of the purified concentration feed stream, in the range of from about 2,000 to about 120,000 ppmw, or in the range of from 3,000 to about 60,000 ppmw.

In one embodiment, the oxidation byproducts in the mother liquor in line 44 and the purified concentration feed stream in line 234 can comprise both BA and non-BA byproducts. As mentioned above, non-BA byproducts include, but are not limited to, isophthalic acid (IPA), phthalic acid (PA), trimellitic acid, 2,5,4'-tricarboxybiphenyl, 2,5,4'-tricarboxybenzophenone, p-TAc, 4-CBA, naphthalene dicarboxylic acid, monocarboxyfluorenones, monocarboxyfluorenes, dicarboxyfluorenes, and/or dicarboxyfluorenones. In one embodiment, the mother liquor in line 44 and the purified concentration feed stream in line 234 can comprise BA in an amount in the range of from about 500 to about 150,000 ppmw based on the weight of the purified concentration feed stream, in the range of from about 1,000 to about 100,000 ppmw, or in the range of from 2,000 to 50,000 ppmw. Additionally, the mother liquor in line 44 and the purified concentration feed stream in line 234 can have a cumulative concentration of non-BA byproducts in the range of from about 500 to about 50,000 ppmw, in the range of from about 1,000 to about 20,000 ppmw, or in the range of from 2,000 to 10,000 ppmw.

In one embodiment of the present invention, less than about 85 weight percent, less than about 50 weight percent, less than about 25 weight percent, less than about 5 weight percent, less than about 3 weight percent, or less than 1 weight percent of the oxidation byproducts in the mother liquor in line 44 are purged from the carboxylic acid production process. In another embodiment, no purge process is employed in the carboxylic acid production process. As used herein, the term "purge process" is defined as any process step or steps that treats a stream containing liquids and/or solids to remove any portion of the oxidation byproducts produced in the carboxylic acid production process in such a way that the removed oxidation byproducts do not exit the carboxylic acid production process with the carboxylic acid product produced therein and/or are not combined with the carboxylic acid product downstream of the carboxylic acid production process.

In one embodiment, the mother liquor in line 44 and the purified concentration feed stream in line 234 can comprise solids in an amount of less than about 5 weight percent, less than about 2 weight percent, or less than 1 weight percent. Additionally, the purified concentration feed stream can have a temperature of less than about 240° C., in the range of from about 20 to about 200° C., or in the range of from 50 to 100° C.

Referring still to FIG. 3, as mentioned above, the purified concentration feed stream can be introduced into concentration zone 236 via line 234. Concentration zone 236 can separate the purified concentration feed stream and optionally the displaced oxidation solvent from line 138a into a catalyst and byproduct rich stream and a solvent rich stream.

Separation in concentration zone 236 can be achieved by any means known in the art that can remove at least a portion of the above-mentioned solvent from the non-solvent components (e.g., catalyst and oxidation byproducts) in the purified concentration feed stream. Examples of suitable equipment for use in concentration zone 236 include, but are not limited to, one or more evaporators. In one embodiment, concentration zone 236 can comprise at least two evaporators. When two evaporators are employed, each one individually can be operated under vacuum at reduced temperature, or can be operated at elevated temperature and pressure. In one embodiment, each evaporator can be operated at a temperature in the range of from about 40 to about 180° C. and a pressure in the range of from about 50 to about 4,500 torr during concentration. Suitable equipment for use as evaporators in concentration zone 236 can include, but is not limited to, a simple agitated and heated tank, a flash evaporator, an advancing front crystallizer, a thin film evaporator, a scraped thin film evaporator, a falling film evaporator, and/or a LIST dryer.

The catalyst and byproduct rich stream can be withdrawn from concentration zone 236 via line 242. In one embodiment, the catalyst and byproduct rich stream in line 242 can have a cumulative concentration of all of the catalyst components and oxidation byproducts that is at least about 2 times, at least about 4 times, or at least 6 times the cumulative concentration of all of the catalyst components and oxidation byproducts in the purified concentration feed stream. The catalyst and byproduct rich stream in line 242 can have a cumulative concentration of all of the catalyst components of at least about 1,000 ppmw, in the range of from about 1,000 to about 120,000 ppmw, in the range of from about 2,000 to about 90,000 ppmw, or in the range of from 3,000 to 60,000 ppmw. Additionally, the catalyst and byproduct rich stream in line 242 can have a cumulative concentration of all of the oxidation byproducts of at least about 2,000 ppmw, in the range of from about 2,000 to about 900,000 ppmw, in the range of from about 4,000 to about 720,000 ppmw, or in the range of from 6,000 to 360,000 ppmw.

In one embodiment of the present invention, at least a portion of the catalyst and byproduct rich stream in line 242 can be routed to purification zone 114 via line 242a. When the catalyst and byproduct rich stream is routed to purification zone 114, the catalyst and byproduct rich stream can be introduced into either or both of the optional crystallization and cooling zones, discussed above in relation to purification zone 114. When the catalyst and byproduct rich stream is routed via line 242a, at least about 80 weight percent, at least about 90 weight percent, or at least 95 weight percent of the catalyst and byproduct rich stream can be introduced into purification zone 114. In one embodiment, substantially all of the catalyst components and oxidation byproducts in the catalyst and byproduct rich stream in line 242a can be introduced into purification zone 114.

In another embodiment, at least a portion of the catalyst and byproduct rich stream in line 242 can be introduced into the purified slurry in line 40 via line 242b. When the catalyst and byproduct rich stream is routed via line 242b, at least about 80 weight percent, at least about 90 weight percent, or at least 95 weight percent of the catalyst and byproduct rich stream can be introduced into line 40. In one embodiment, substantially all of the catalyst components and oxidation byproducts in the catalyst and byproduct rich stream in line 242b can be introduced into line 40.

In another embodiment, at least a portion of the catalyst and byproduct rich stream in line 242 can be introduced into product isolation zone 100 via line 242c. When the catalyst and byproduct rich stream is routed via line 242c, at least about 80 weight percent, at least about 90 weight percent, or at least 95 weight percent of the catalyst and byproduct rich stream can be introduced into product isolation zone 100. In one embodiment, substantially all of the catalyst components and oxidation byproducts in the catalyst and byproduct rich stream in line 242c can be introduced into product isolation zone 100.

The above-mentioned solvent rich stream can be withdrawn from concentration zone 236 via line 244. In one embodiment, the solvent rich stream can have a higher concentration of solvent than the concentration of solvent in the purified concentration feed stream in line 234. At least a portion of the solvent rich stream can be routed to oxidation zone 110 via line 244. In one embodiment, at least about 80 weight percent, at least about 90 weight percent, or at least 95 weight percent of the solvent rich stream in line 244 can be routed to oxidation zone 110.

FIG. 4 illustrates an embodiment of the present invention where a portion of the mother liquor in line 44 can be withdrawn via line 302 to form a purified byproduct removal feed. The composition of the purified byproduct removal feed can be substantially the same as the composition of the purified concentration feed stream in line 234, as discussed above with reference to FIG. 3. The purified byproduct removal feed can be introduced into non-BA byproduct removal zone 304 via line 302. Additionally, a portion of the displaced oxidation solvent from purification zone 114 can be routed to non-BA byproduct removal zone 304 via line 138a or, alternatively, can be combined with the purified byproduct removal feed prior to introduction into non-BA byproduct removal zone 304. In another embodiment, at least a portion of the remaining mother liquor in line 44 can be routed, either directly or indirectly, to oxidation zone 110 via line 340. Optionally, at least a portion of the wash liquor in line 46 can be combined with at least a portion of the mother liquor in line 340 prior to introduction into oxidation zone 110.

Non-BA byproduct removal zone 304 can separate the purified byproduct removal feed into a solvent rich stream, a catalyst and BA rich stream, and a non-BA byproduct rich stream. The catalyst and BA rich stream can be withdrawn from non-BA byproduct removal zone 304 via line 306. In one embodiment, the catalyst and BA rich stream can have a cumulative concentration of all of the catalyst components and BA that is at least about 2 times, at least about 4 times, or at least 6 times the cumulative concentration of all of the catalyst components and BA in the purified byproduct removal feed. The catalyst and BA rich stream in line 306 can have a cumulative concentration of all of the catalyst components of at least about 1,000 ppmw, in the range of from about 1,000 to about 120,000 ppmw, in the range of from about 2,000 to about 90,000 ppmw, or in the range of from 3,000 to 60,000 ppmw. Additionally, the catalyst and BA rich stream in line 306 can have a concentration of BA of at least about 1,000 ppmw, in the range of from about 1,000 to about 900,000 ppmw, in the range of from about 2,000 to about 600,000 ppmw, or in the range of from 4,000 to about 300,000 ppmw.

In one embodiment, at least a portion of the catalyst and BA rich stream can be routed to optional BA oxidizer 308, where at least a portion of the BA in the catalyst and BA rich stream can be oxidized. BA oxidizer 308 can be any oxidation reactor known in the art capable of reducing the amount of BA in the catalyst and BA rich stream by at least about 10 weight percent, at least about 25 weight percent, or at least 50 weight percent.

An optionally oxidized catalyst and BA rich stream can be withdrawn from BA oxidizer 308 via line 310. The oxidized catalyst and BA rich stream in line 310 can have a concentration of BA in the range of from about 900 to about 810,000 ppmw, in the range of from about 1,500 to about 450,000 ppmw, or in the range of from 2,000 to 150,000 ppmw. At least a portion of the optionally oxidized catalyst and BA rich stream can be routed to oxidation zone 110 via line 310. In one embodiment, at least about 80 weight percent, at least about 90 weight percent, or at least 95 weight percent of the optionally oxidized catalyst and BA rich stream in line 310 can be introduced into oxidation zone 110.

The non-BA byproduct rich stream can be withdrawn from non-BA byproduct removal zone via line 312. In one embodiment, the non-BA byproduct rich stream can have a cumulative concentration of non-BA byproducts that is at least about 2 times, at least about 4 times, or at least about 6 times the cumulative concentration of non-BA byproducts in the purified byproduct removal feed. The non-BA byproduct rich stream in line 312 can have a cumulative concentration of non-BA byproducts of at least about 10 weight percent, in the range of from about 10 to about 95 weight percent, in the range of from about 20 to about 90 weight percent, or in the range of from 30 to about 85 weight percent.

The non-BA byproduct rich stream in line 312 can be in the form of a wet cake. In one embodiment, the non-BA byproduct rich stream in line 312 can comprise liquid in an amount in the range of from about 5 to about 30 weight percent, in the range of from about 10 to about 25 weight percent, or in the range of from about 12 to about 23 weight percent.

Optionally, the non-BA byproduct rich stream in line 312 can be introduced into drying zone 314. Drying zone 314 can comprise any drying device known in the art that can produce a dried non-BA byproduct rich stream comprising less than about 5 weight percent liquid, less than about 3 weight percent liquid, or less than 1 weight percent liquid. The dried non-BA byproduct rich stream can be discharged from drying zone 314 via line 316.

In another embodiment, the non-BA byproduct rich stream in line 312 can optionally be introduced into solvent swap zone 318 to produce a wet non-BA byproduct rich stream. Solvent swap zone 318 can operate to replace at least a portion of the liquid in the non-BA byproduct rich stream with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with counter current washing. The wet non-BA byproduct rich stream can be discharged from solvent swap zone 318 via line 320. The wet non-BA byproduct rich stream can comprise in the range of from about 5 to about 30 weight percent liquid, in the range of from about 10 to about 25 weight percent liquid, or in the range of from 12 to 23 weight percent liquid.

In one embodiment of the present invention, at least a portion of the non-BA byproduct rich stream can be combined with the isolated product in line 52, the dried isolated product in line 124, and/or the wet isolated product in line 128. In one embodiment, at least about 80 weight percent, at least about 90 weight percent, at least 95 weight percent, or substantially all of the non-BA byproducts in the non-BA byproduct rich stream can be combined with the isolated product in line 52, the dried isolated product in line 124, and/or the wet isolated product in line 128.

The solvent rich stream produced in non-BA byproduct removal zone 304 can be withdrawn via line 322. The solvent rich stream in line 322 can have a higher concentration of solvent than the concentration of solvent in the purified byproduct removal feed stream in line 302. In one embodiment, at least a portion of the solvent rich stream generated in non-BA byproduct removal zone 304 can be routed to oxidation zone 110 via line 322. At least about 80 weight percent, at least about 90 weight percent, or at least 95 weight percent of the solvent rich stream in line 322 can be introduced into oxidation zone 110.

In one embodiment of the present invention, non-BA byproduct removal zone 304 can comprise a concentration section (not shown) and a solid/liquid separation section (not shown). In this embodiment, the concentration section in non-BA byproduct removal zone 304 can operate to remove at least a portion of the solvent in the purified byproduct removal feed, thereby forming the above-mentioned solvent rich stream. The concentration section in non-BA byproduct removal zone 304 can remove at least about 30, at least about 45, or at least 60 weight percent of the solvent in the purified byproduct removal feed.

In one embodiment, a concentrated byproduct removal stream (not shown) can be discharged from the concentration section in non-BA byproduct removal zone 304. The concentrated byproduct removal stream can have a cumulative concentration of non-solvent components (e.g., catalyst components and oxidation byproducts) that is at least about 2 times, at least about 4 times, or at least 6 times the cumulative concentration of non-solvent components in the purified byproduct removal feed stream. The concentrated byproduct removal stream can have a cumulative concentration of all of the catalyst components of at least about 1,000 ppmw, in the range of from about 1,000 to about 120,000 ppmw, in the range of from about 2,000 to about 90,000 ppmw, or in the range of from 3,000 to 60,000 ppmw. Additionally, the concentrated byproduct removal stream can have a cumulative concentration of oxidation byproducts of at least about 2,000 ppmw, in the range of from about 2,000 to about 900,000 ppmw, in the range of from about 4,000 to about 720,000 ppmw, or in the range of from 6,000 to 360,000 ppmw.

The concentrated byproduct removal stream can be introduced into the above-mentioned solid/liquid separation section in non-BA byproduct removal zone 304. The solid/liquid separation section can separate the concentrated byproduct removal stream into a predominately fluid phase catalyst and BA rich mother liquor and a wet cake. In one embodiment, the above-mentioned non-BA byproduct rich stream can comprise at least a portion of the wet cake. Additionally, the above mentioned catalyst and BA rich stream can comprise at least a portion of the predominately fluid phase catalyst and BA rich mother liquor.

FIG. 5 illustrates an embodiment of the present invention where the crude slurry in line 112 can be treated in purification zone 114 to thereby produce a displaced oxidation solvent stream and a purified slurry. The purified slurry can be withdrawn from purification zone 114 via line 40, and the displaced oxidation solvent stream can be withdrawn via line 138. In the embodiment of FIG. 5, at least about 80 weight percent, at least about 90 weight percent, or at least 95 weight percent of the displaced oxidation solvent stream in line 138 can be routed, either directly or indirectly, to oxidation zone 110.

In one embodiment of the present invention, at least a portion of the purified slurry in line 116 can be employed as a concentration feed stream. In one embodiment, the concentration feed stream can be introduced into concentration zone 402. Concentration zone 402 can separate the concentration feed stream into a solvent rich stream and a concentrated isolation feed stream.

Separation in concentration zone 402 can be achieved by any means known in the art that can remove at least a portion of the solvent from the purified slurry. Examples of suitable equipment for use in concentration zone 402 include, but are not limited to, one or more evaporators. In one embodiment, concentration zone 402 can comprise at least two evaporators. When two evaporators are employed, each one individually can be operated under vacuum at reduced temperature, or can be operated at elevated temperature and pressure. In one embodiment, each evaporator can be operated at a temperature in the range of from about 40 to about 180° C. and a pressure in the range of from about 50 to about 4,500 torr during concentration. Suitable equipment for use as evaporators in concentration zone 402 can include, but is not limited to, a simple agitated and heated tank, a flash evaporator, an advancing front crystallizer, a thin film evaporator, a scraped thin film evaporator, a falling film evaporator, and/or a LIST dryer.

The solvent rich stream can be withdrawn from concentration zone 402 via line 404. The solvent rich stream in line 404 can have a concentration of solvent that is at least about 1.1 times, at least about 1.3 times, or at least 1.5 times the concentration of solvent in the purified slurry in line 116. In one embodiment, at least a portion of the solvent rich stream in line 404 can be routed to oxidation zone 110. At least about 80 weight percent, at least about 90 weight percent, or at least 95 weight percent of the solvent rich stream in line 404 can be routed to oxidation zone 110.

The concentrated isolation feed stream can be withdrawn from concentration zone 402 via line 40. In one embodiment, the concentrated isolation feed stream in line 40 can have a concentration of oxidation byproducts that is at least about 1.05 times, at least about 1.2 times, or at least 1.4 times the concentration of oxidation byproducts in the concentration feed stream. Additionally, the concentrated isolation feed stream in line 40 can have a cumulative concentration of oxidation byproducts of at least about 1,050 ppmw, in the range of from about 1,050 to about 280,000 ppmw, in the range of from about 2,100 to about 168,000 ppmw, or in the range of from about 3,150 to about 84,000 ppmw.

The concentrated isolation feed stream in line 40 can have a concentration of solids that is at least about 1.05 times, at least about 1.2 times, or at least 1.4 times the concentration of solids in the concentration feed stream. Furthermore, the concentrated isolation feed stream in line 40 can comprise solids in an amount in the range of from about 20 to about 70 weight percent, in the range of from 25 to 60 weight percent, or in the range of from 30 to 50 weight percent.

In one embodiment of the present invention, the concentrated isolation feed stream in line 40 can be employed as the isolation feed slurry introduced into product isolation zone 100. Product isolation zone 100 can separate the concentrated isolation feed stream into a mother liquor, a wash liquor, and an isolated product in substantially the same manner as discussed above with reference to FIG. 1. In the embodiment of FIG. 5, at least about 80 weight percent, at least about 90 weight percent, or at least 95 weight percent of the mother liquor produced in product isolation zone 100 can be routed via line 44 to oxidation zone 110. Additionally, at least about 80 weight percent, at least about 90 weight percent, or at least 95 weight percent of the wash liquor produced in product isolation zone 100 can be routed via line 46 to oxidation zone 110. The isolated product can be discharged via line 52, as discussed above with reference to FIG. 1.

It will be understood by one skilled in the art that each of the above-described embodiments, as well as any sub-parts of those embodiments, may be operated in a continuous or a non-continuous manner. Non-continuous operations include, but are not limited to, batch-wise operations, cyclical operations, and/or intermittent operations. Additionally, it will be understood that two or more of the above embodiments may be used in combination. For example, in a carboxylic acid production process, a concentration step may be employed both before and after the product isolation step.

In some of the embodiments above, temperature ranges are provided for a specified operation. For each of the above embodiments where a temperature range is provided, the temperature is defined as the average temperature of the substance in the given zone or section. By way of illustration, as discussed above with reference to FIG. 3, the purified concentration feed stream can be treated in concentration zone 236, where the evaporators in concentration zone 236 can be operated at a temperature in the range of from about 40 to about 180° C. This means that the average temperature of the purified concentration feed stream while in the evaporators in concentration zone 236 can be in the range of from about 40 to about 180° C.

Numerical Range

The present description uses numerical ranges to quantify certain parameters relating to the invention. It should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds).

DEFINITIONS

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Claim not Limited to Disclosed Embodiments

The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A process for producing purified terephthalic acid (PTA), said process comprising: (a) oxidizing an aromatic compound in an oxidation zone to thereby produce a crude slurry comprising crude terephthalic acid (CTA) particles; (b) subjecting at least a portion of said crude slurry to purification to thereby produce a purified slurry comprising PTA particles, oxidation byproducts, and an aliphatic acid in an amount of at least about 10 weight percent; and (c) isolating at least a portion of said PTA particles from said purified slurry in a product isolation zone to thereby produce a PTA product, wherein said product isolation zone is defined within a rotary pressure drum filter, wherein the cumulative rate at which said oxidation byproducts exit said PTA production process with said PTA product and/or are combined with said PTA product downstream of said PTA production process is at least about 15 percent of the net make rate of said oxidation byproducts in said PTA production process.

2. The process of claim 1, wherein said aliphatic acid comprises an aliphatic carboxylic acid having 1 to 6 carbon atoms.

3. The process of claim 1, wherein said aliphatic acid comprises acetic acid.

4. The process of claim 1, wherein said purified slurry comprises a liquid phase, wherein said liquid phase comprises said aliphatic acid in an amount of at least about 60 weight percent.

5. The process of claim 1, wherein the cumulative rate at which said oxidation byproducts exit said PTA production process with said PTA product and/or are combined with said PTA product downstream of said PTA production process is at least about 40 percent of the net make rate of said oxidation byproducts in said PTA production process.

6. The process of claim 1, wherein said oxidizing of step (a) comprises a precipitating oxidation reaction that forms said CTA particles.

7. The process of claim 6, wherein said aromatic compound comprises para-xylene, wherein said precipitating oxidation reaction causes at least about 10 weight percent of said para-xylene to form solids in said oxidation zone.

8. The process of claim 1, wherein said isolating of step (c) further produces a mother liquor comprising a solvent, one or more catalyst components, and oxidation byproducts, wherein said oxidation byproducts comprise benzoic acid (BA) and non-BA byproducts.

9. The process of claim 8, further comprising treating at least a portion of said mother liquor in a concentration zone to thereby produce a catalyst and oxidation byproduct rich stream and a solvent rich stream.

10. The process of claim 9, further comprising directly or indirectly routing at least a portion of said solvent rich stream to said oxidation zone, and/or directly or indirectly routing at least a portion of said catalyst and oxidation byproduct rich stream to a purification zone where said purification of step (b) is carried out and/or to said product isolation zone.

11. The process of claim 8, further comprising treating at least a portion of said mother liquor in a non-BA byproduct removal zone to thereby produce a non-BA byproduct rich stream, a solvent rich stream, and a catalyst and BA rich stream.

12. The process of claim 11, further comprising directly or indirectly routing at least a portion of said solvent rich stream and/or at least a portion of said catalyst and BA rich stream to said oxidation zone, and/or routing at least a portion of said non-BA byproduct rich stream to one or more locations that causes at least a portion of said non-BA byproducts present in said non-BA byproduct rich stream to be combined with said PTA product downstream of said PTA production process.

13. A method for treating a purified slurry comprising purified terephthalic acid (PTA) particles, said method comprising: treating said purified slurry in a catalyst removal zone to thereby produce a wet cake comprising at least a portion of said PTA particles and a mother liquor, wherein said slurry comprises said PTA particles in an amount of at least about 15 weight percent, wherein said slurry comprises acetic acid, and wherein said catalyst removal zone is defined within a rotary pressure drum filter.

14. The method of claim 13, wherein said purified slurry comprises oxidation byproducts produced in a terephthalic acid (TPA) production process.

15. The method of claim 14, wherein said oxidation byproducts exit said TPA production process with said wet cake at substantially the same rate as the make rates of said oxidation byproducts in said TPA production process.

16. The method of claim 14, further comprising routing at least a portion of said mother liquor to an oxidation section where at least a portion of said oxidation byproducts are formed.

17. The method of claim 13, wherein said mother liquor comprises a solvent comprising acetic acid and/or water.

18. The method of claim 17, further comprising concentrating at least a portion of said purified slurry in a concentration section prior to said treating in said catalyst removal zone and/or treating at least a portion of said mother liquor in a concentration section to thereby produce a solvent rich stream and a concentrated stream.

19. The method of claim 18, further comprising routing at least a portion of said concentrated stream to a post-oxidation section where at least a portion of said PTA particles are formed and/or routing at least a portion of said concentrated stream to said catalyst removal zone.

20. The method of claim 13, further comprising subjecting a crude slurry comprising crude terephthalic acid (CTA) particles to oxidative digestion to thereby produce said purified slurry.

21. The method of claim 13, further comprising introducing a wash stream into said catalyst removal zone to wash at least a portion of said wet cake thereby producing a washed wet cake and a wash liquor.

* * * * *